United States Patent
You et al.

(10) Patent No.: US 6,176,120 B1
(45) Date of Patent: *Jan. 23, 2001

(54) METHODS OF ANALYZING WATER SOLUBLE CONTAMINANTS GENERATED DURING MICROELECTRONIC DEVICE MANUFACTURING PROCESSES

(75) Inventors: Nam-hee You, Kyungki-do; Dong-soo Lee, Seoul; Sun-young Lee; Jung-sung Hwang, both of Kyungki-do, all of (KR)

(73) Assignee: Samsung Electronics Co., Ltd. (KR)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/330,972

(22) Filed: Jun. 11, 1999

Related U.S. Application Data

(62) Division of application No. 09/048,552, filed on Mar. 26, 1998, now abandoned.

(30) Foreign Application Priority Data

May 28, 1997 (KR) .................................................. 97-21338

(51) Int. Cl.[7] .......................... G01N 11/00; E03B 11/00; B09B 1/00
(52) U.S. Cl. ......................... 73/53.01; 405/128; 210/170
(58) Field of Search ................................ 73/53.01, 23.2, 73/23.22, 23.35, 28.01, 31.03, 53.07, 61.52; 405/128; 166/267, 370; 210/170, 747

(56) References Cited

U.S. PATENT DOCUMENTS

| | | | |
|---|---|---|---|
| 3,440,865 | 4/1969 | Gamson | 73/53.01 |
| 3,584,674 | 6/1971 | Nolan et al. | 73/61.77 |
| 3,726,063 | 4/1973 | Magorien et al. | 96/200 |
| 4,012,278 | 3/1977 | Mostofin et al. | 73/61.77 |
| 4,556,538 | * 12/1985 | Matsushita et al. | 422/70 |
| 5,441,365 | 8/1995 | Duffney et al. | 405/128 |

FOREIGN PATENT DOCUMENTS 2 304 891   3/1997   (GB) .............................. G01N/1/22

* cited by examiner

*Primary Examiner*—Hezron Williams
*Assistant Examiner*—Jay L. Politzer
(74) *Attorney, Agent, or Firm*—Myers Bigel Sibley & Sajovec

(57) ABSTRACT

Methods of analyzing water-soluble contaminants comprise providing reference air streams having gaseous water present therein; condensing the reference air streams such that the gaseous water liquefies; pressurizing the liquefied water; and supplying the liquefied water to analyzers. Systems for analyzing water-soluble contaminants comprise air inlets that absorb reference air containing gaseous water therein; valves that control the flow of the reference air in fluid communication with the air inlets; condensers that condense the gaseous water in the reference air in fluid communication with the valves; pressurization pumps that pressurize the water condensed from the reference air in fluid communication with the condensers; and discharge pumps that discharge an excessive amount of water contained in the reference air.

21 Claims, 3 Drawing Sheets

METHODS OF ANALYZING WATER SOLUBLE CONTAMINANTS GENERATED DURING MICROELECTRONIC DEVICE MANUFACTURING PROCESSES

CROSS-REFERENCE TO RELATED APPLICATIONS

The instant application is a divisional application of U.S. Ser. No. 09/048,552 filed Mar. 26, 1998 abandoned the disclosure of which is incorporated by reference herein in its entirety.

FIELD OF THE INVENTION

The invention generally relates to the analysis of contaminants generated during microelectronic device processing.

BACKGROUND OF THE INVENTION

It is typically necessary to control the level of contaminants in a cleanroom such that microelectronic device processing may be effectively carried out. An example of a common contaminant is floating dust. Other conditions within the cleanroom, such as those relating to noise, vibration, temperature, and light intensity, may also be controlled such that optimum processing conditions may be obtained.

Regulating dust levels, temperature, and humidity in a cleanroom is especially important during integrated circuit (e.g., semiconductor) device fabrication design layout. Design layout typically encompasses a number of operations relating to, for example, pattern formation in water fabrication, inspection, assembly/packaging, final testing, and quality testing. In particular, wafer fabrication usually involves repetitive process steps such as diffusion, exposure, development, etching, and diffusion. Specifically, equipment and materials involved in these process steps should not be contaminated in order to potentially obtain maximum microelectronic device production yield, precision, and reliability.

In a typical processing operation, air entering the cleanroom is usually filtered in order to attempt to remove the contaminants, and the air is then typically circulated throughout the cleanroom. Although it may be possible to achieve a certain level of air cleanliness, it is often extremely difficult to achieve an extremely high cleanliness level by only employing the above filtering system. Although the level of cleanliness attained by using a conventional filtering system may be adequate for certain processes, a higher degree of cleanliness is often desirable.

The presence of water-soluble contaminants, such as those resulting from wet fabrication processing, often adversely affect production yield and integrated circuit device operation. For example, the presence of water-soluble ionic materials on wafer surfaces may haze or blur the surfaces and distort corresponding photoresists. Moreover, the ionic materials are capable of functioning as dopants which can negatively impact diffusion processes containing these materials.

In view of the above, it would be desirable to control the level of water-soluble contaminants which may be present in a cleanroom. Conventionally, cleanroom cleanliness is typically controlled by monitoring the total number of particles present in the cleanroom atmosphere irrespective of the water solubility of the particles. The solubility of the particles is often measured by techniques involving the use of a as denuder, chemiluminescence, or fluoroluminescence.

FIG. 1 illustrates a conventional denuder. As shown, the denuder comprises an inlet 11 which may be connected to an inlet tube (not shown) capable of taking reference air for analysis from various directions. An impactor 12 is also present and is equipped with an impact plate 13. The denuder also includes a diffusion denuder 14, an after filter 15, and a sampling pump 16. Collected air typically collides with the impact plate 13 of the impactor 12 to thereby separate from the particles, and subsequently form microparticles which are not separated by impactor 12. More specifically, polar molecules such as $SO_2$, $NO_2$, or $NH_3$ are separated inside the diffusion denuder 14 composed of stainless steel. The polar molecules are then typically supplied to the sampling pump through filter 15 such that a sample for analysis may be obtained. Notwithstanding any potential advantage, the conventional denuder typically is not able to separately analyze water-soluble materials which may be present in the reference air.

A conventional chemiluminescent method typically involves chemically reacting materials to be analyzed and then analyzing any light which may be emitted by the materials as a result of the chemical reaction typically initiated by using a photo-amplified tube. According to the chemiluminescent method, a radiation impulse (e.g., ultraviolet rays) is applied, and the material typically yields a luminsecence which is subsequently analyzed. The chemiluminescent method, however, may be disadvantageous in that only one component is typically analyzed at a time. Thus, the technique is often inefficient.

In addition to the above, samples have been collected and analyzed by conventional spectroscopic analyzers. In particular, these techniques may be carried out by using a Jar method, an Impinger method, and the like.

The Jar method typically involves exposing a jar containing deionized water to the atmosphere such that water-soluble contaminants are able to dissolve therein. The water-soluble contaminants are then subsequently analyzed. Although the structure and application of the jar are relatively simple, the above may be undesirable in that collection times are typically long. As a result, collection efficiency may be inaccurate. Although a post collection treatment is often employed in conjunction with this apparatus, it still may be difficult to obtain an accurate measurement of the contaminants.

The Impinger method typically involves spraying an air sample toward water or another liquid which is used as a collection source. The above operation is usually carried out by using a double tube or an gas collector impinger. The contaminants contained within the air are collected by the water or other liquid and then are subsequently analyzed. Although the apparatus used in the Impinger method is relatively simple, the method is potentially disadvantageous in that an additional treatment step is often required prior to contaminant analysis.

There is a need in the art for systems (apparatus) and methods for analyzing water-soluble contaminants which address the problems often associated with conventional analysis techniques.

SUMMARY OF THE INVENTION

In attempting to address the problems noted above, in one aspect the invention provides methods of analyzing water-soluble contaminants. The methods comprise providing reference air streams having gaseous water present therein; condensing the reference air streams such that the gaseous water liquefies; pressurizing the liquefied water; and supplying the liquefied water to an analyzer.

In another aspect, the invention provides systems (apparatus) for analyzing water-soluble contaminants. The systems comprise air inlets that absorb reference air containing gaseous water therein; valves that control the flow of the reference air which are in fluid communication with the air inlets; condensers that condense the gaseous water in the reference air, the condensers being in fluid communication with the valves; pressurization pumps that pressurize the water condensed from the reference air, the pressurization pumps being in fluid communication with the condensers; and discharge pumps that discharge excess water contained in the reference air, the discharge pumps being in fluid communication with the condensers.

The present invention may be advantageous in that water-soluble contaminants may be analyzed with a higher level of reliability in comparison to conventional techniques.

DETAILED DESCRIPTION OF THE PREFERRED EMBODIMENTS

Figure 1:
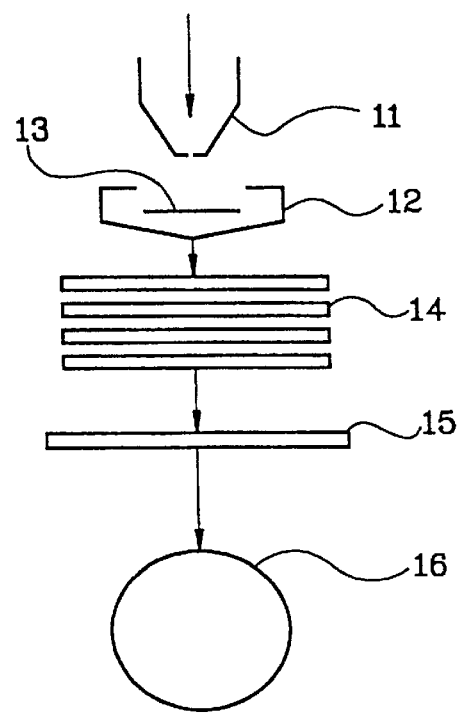
FIG. 1 is a schematic representation of a conventional denuder.

The present invention now will be described more fully hereinafter with reference to the accompanying drawings and examples, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

In one aspect, the invention relates to methods for analyzing water-soluble contaminants. The methods comprise contacting reference air streams containing gaseous water such that water which is present in the reference air streams liquefies, pressurizing the liquefied water, and supplying the liquefied water to analyzers.

Typically, the step of contacting the reference air streams involves contacting the air streams with the surfaces of condensers. It is preferable that the condenser surfaces are maintained at low temperatures so as to reduce the saturated vapor pressure of the reference air streams. As a result, the gaseous water in the reference air streams may liquefy, typically into water drops. In this step, water-soluble contaminants may be solubilized in the liquefied water and thus qualitative and quantitative analyses of the water-soluble contaminants are made possible. In addition to the above, these method may allow for only a limited amount of water to condense from the reference air stream. As such, the water typically does not need to be treated prior to analysis, and thus the water may be able to be sent directly to the analyzer.

Various analyzers may be used in the methods of the invention. It is preferred that an ion-exchange chromatographer is employed.

Preferably, the methods further comprise the step of maintaining the reference air streams at constant temperatures prior to condensing gaseous water contained therein. Preferably, the temperatures of the reference air streams are maintained from about 20° C. to about 40° C.

If desired, the methods may further comprise the step of controlling the humidity of the reference air streams. Known means may be used to control the humidity. For example, the humidity may be controlled by means which are employed in controlling the temperatures of the reference air streams. Since it is known that humidity varies with temperature, it is preferable to keep the temperature constant in order to be able to maintain the humidity at constant levels. In particular, it is believed that when the temperature of the reference air streams are lower than 20° C. or higher than 40° C., the humidity of the reference air streams may vary too widely, and thus may be difficult to control. Accordingly, it may be difficult to achieve an accurate quantitative analysis of the water-soluble contaminants.

It is preferred that the humidity of the reference air be controlled from between about 30% to about 90%. If the humidity falls below 30%, insufficient amounts of liquefied water are obtained for analysis. If the humidity is above 90%, excessive levels of water may be generated which typically causes errors in water-contaminant analysis. More preferably, the humidity is controlled in the range of about 35% to about 60%, and most preferably, the humidity is controlled from about 40% to about 50%.

Figure 2:
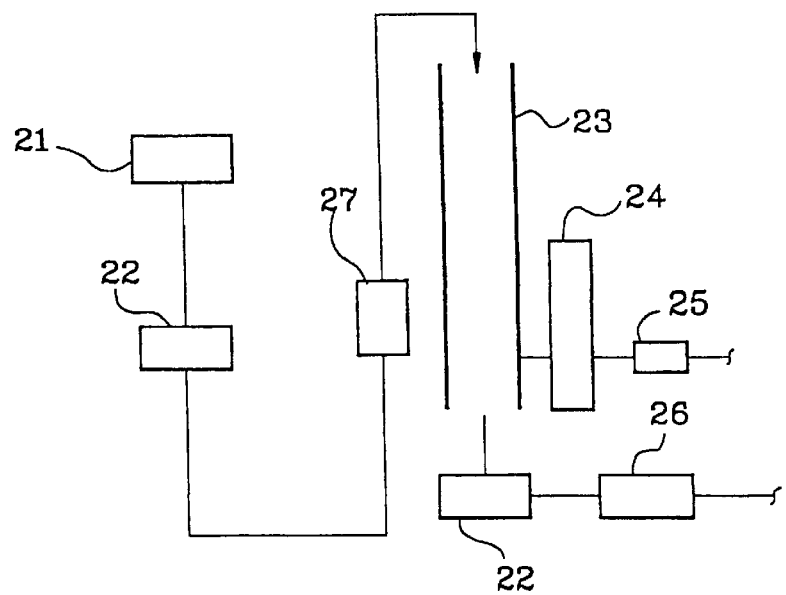
FIG. 2 is a schematic representation of one embodiment of a system in accordance with the invention.

The invention will now be further described in reference to the accompanying drawings. FIG. 2 illustrates a system (apparatus) for analyzing water-soluble contaminants. The apparatus comprises an air inlet 21 that absorbs reference air; a flow control valve 22 that controls the flow of the reference air, the flow control valve being in fluid communication with the air inlet; a condenser 23 that condenses water present in the reference air, the condenser being in fluid communication with the flow control valve; and a pressurization pump 24 that pressurizes the water condensed from the reference air in fluid communication with the condenser so as to supply the condensed water into an analyzer 25. In addition, a discharge pump 26 may be employed to discharge excess water contained in the reference air (water not directed to the analyzer 25). The discharge pump 26 is in fluid communication with condenser 23 via flow control valve 22.

The air inlet 21 is typically used to absorb the reference air to be analyzed. The reference air may supplied in various ways. As an example, the reference air may be induced from the atmosphere. The reference air is eventually supplied to condenser 23. In general, conventional absorbing means are employed such that a turbulent air stream is generated by using a conventional driving motor and impeller with the rotation of the impeller positioned in a specified direction. Alternatively, the absorbing means may comprise a conventional vacuum motor and an absorbing hose. This is able to generate a turbulent air stream by virtue of the formation of a vacuum pump.

The flow control valve 22 is present to control the flow of the reference air, and thus the amount of reference air which enters the condenser. Various types of valves may be used. Typically, a conventional MFC (mass flow controller) valve is employed.

The analyzer 25 functions to analyze 25 the liquefied water which condenses from the reference air. Various systems can be used as analyzer. Preferably, an ion chromatographer is used to analyze the water-soluble contaminants contained in the liquefied water. The analyzer 25 may be selected according to the species of water-soluble contaminants to be evaluated. Thus, the types of analyzers which may be used are numerous and known to one skilled in the art.

Figure 3:
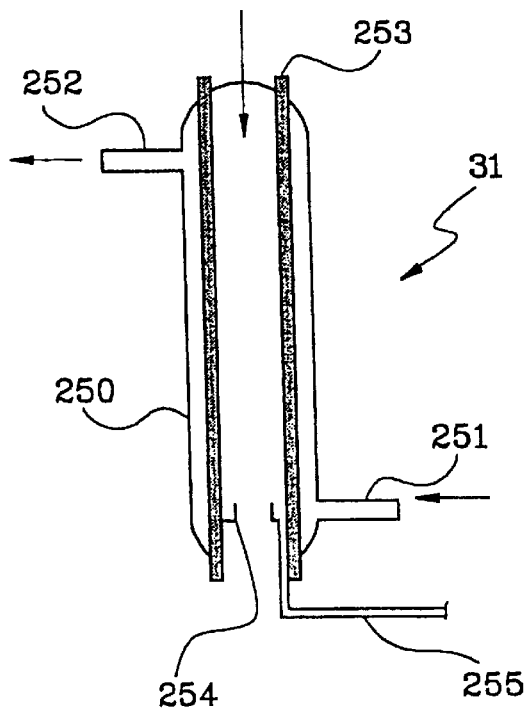
FIG. 3 is a schematic representation of one embodiment of a condenser present in the system illustrated in FIG. 2.
Figure 4:
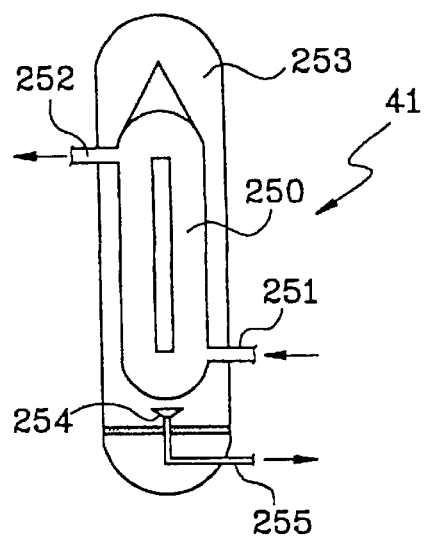
FIG. 4 is a schematic representation of a second embodiment of a condenser present in the system illustrated in FIG. 2.
Figure 5:
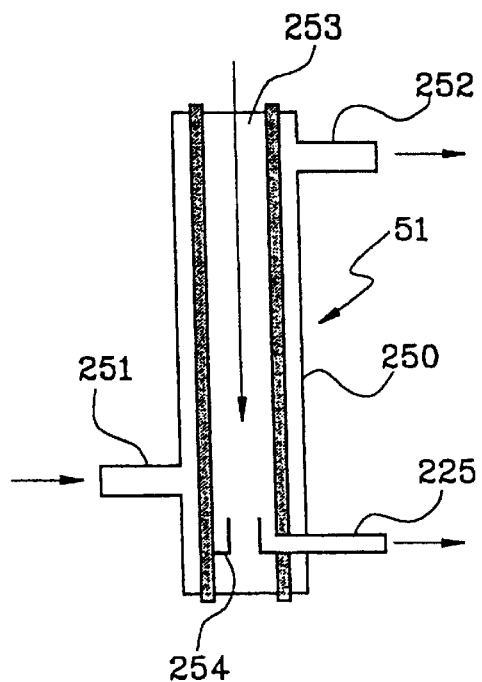
FIG. 5 is a schematic representation of a third embodiment of a condenser present in the system illustrated in FIG. 2.

Referring now to FIGS. 3–5, a condenser 23 is illustrated. As shown, the condenser 23 comprises a cooling medium tube 250 which serves to condense gaseous water present in the reference air. Cooling medium tube 250 comprises a cooling medium inlet 251 and cooling medium outlet 252 which allows the cooling medium (e.g., water) to be maintained at a low temperature due to its circulation through tube 250. The condenser further comprises a reference air tube 253 that passes reference air therethrough, a collector 254 that collects water which has condensed from the reference air, and a water outlet 255 that discharges the collected water from condenser 23. Preferably, the cooling medium is maintained at a temperature ranging about 0° C. to about 10° C. ("low temperature").

In particular, cooling medium tube 250 is constructed so as to allow for cooling medium to circulate in a continuous manner. Tube 250 may be maintained at a low temperature by virtue of the surface of the tube 250 coming in contact with the cooling medium.

Reference air tube 253 is configured to allow reference air to flow therethrough and contact the surface of cooling medium tube 250. Because the reference air flows through cooling medium tube 250, the reference air itself is able to reduce in temperature by contacting the surface of cooling medium tube 250 which is preferably maintained at a low temperature (e.g., from about 0° C. to about 10° C.). In particular, it is especially advantageous to maintain the vapor pressure of the reference air at a sufficiently low level such that the most of the gaseous water is able to condense inside cooling medium tube 250.

Typically, the collector 254 is present near the end of cooling medium tube 250. The collector 254 serves to collect water which is formed on the surface of the cooling medium tube 250.

Water outlet 255 is connected to collector 254 and allows for the discharge of collected water from condenser 23. A conventional tube is typically employed as water outlet 255, and is typically directly connected to pressurization pump 24 which transports the water to analyzer 25.

In one embodiment, condenser 23 may be configured such that the cooling medium tube 250 surrounds reference air tube 253, in which instance it is referred to as an "internal condensing condenser" (denoted as 31). The term "internal condensing condenser" refers to condensation taking place inside cooling medium tube 250.

In another embodiment, condenser 23 may be configured such that the reference air tube 253 surrounds cooling medium tube 250, in which instance it is referred to as an "outer condensing condenser" (denoted as 41). The term "outer condensing condenser" refers to condensation taking place outside the cooling medium tube 250.

Typically, the condenser 23 is structured such that its cooling medium tube 250 and its reference air tube 253 are formed in series. In such an embodiment, condenser 23 has a planar-type accumulation structure, i.e., a "planar-type condenser". A planar-type condenser refers to cooling medium tuber 250 and reference air tube 253 being planar-type in that they face each other and are connected in series.

Internal-condensing condenser 31, outer-condensing condenser 41, and planar type condenser 51 each include cooling medium tube 250, reference air tube 253, collector 254, and outlet 255. Cooling medium inlet 251 and cooling medium outlet 252 are also included in the embodiments denoted by 31, 41, and 51.

Various materials may be used as cooling mediums in the invention. Typically, water is employed since it typically has a favorable latent heat and is relatively inexpensive. Moreover, it may present potentially few environmental risks to humans relative to other materials.

A number of different pumps may be used for pressurization pump 24. Preferably, a peristaltic pump is employed. An especially suitable peristaltic pump is constructed such that the fluid inside the tube is compressed by the peristaltic movement of the tube by virtue of the pressure applied externally. In the peristaltic pump, the fluid typically is not contacted with other parts except the tube, and the fluid is often directly compressed inside the tube. By virtue of employing a peristaltic pump, little water loss or contamination thereof may be experienced.

As alluded to herein, an ion-exchange chromatographer is preferably used as analyzer 25. The ion-exchange chromatographer typically uses an ion-exchanger as a stationary phase which serves to separate the ions by virtue of the differences in ion speed influenced by the difference in the ion-exchange adhesiveness.

As illustrated, the system of the invention may further include a controller 27 that controls the humidity of the reference air. In one embodiment, the humidity controller 27 comprises a humidifier and a dehumidifier. The humidifier supplies water to the reference air so as to increase the humidity of the air. As a result, water-soluble contaminants contained in the reference air are solubilized in the water, and thus removed from the reference air. If the humidity of the reference air is excessive, the dehumidifier may serve to reduce the quantity of water in the reference air such that the amount of water introduced into the analyzer is decreased.

Figure 6:
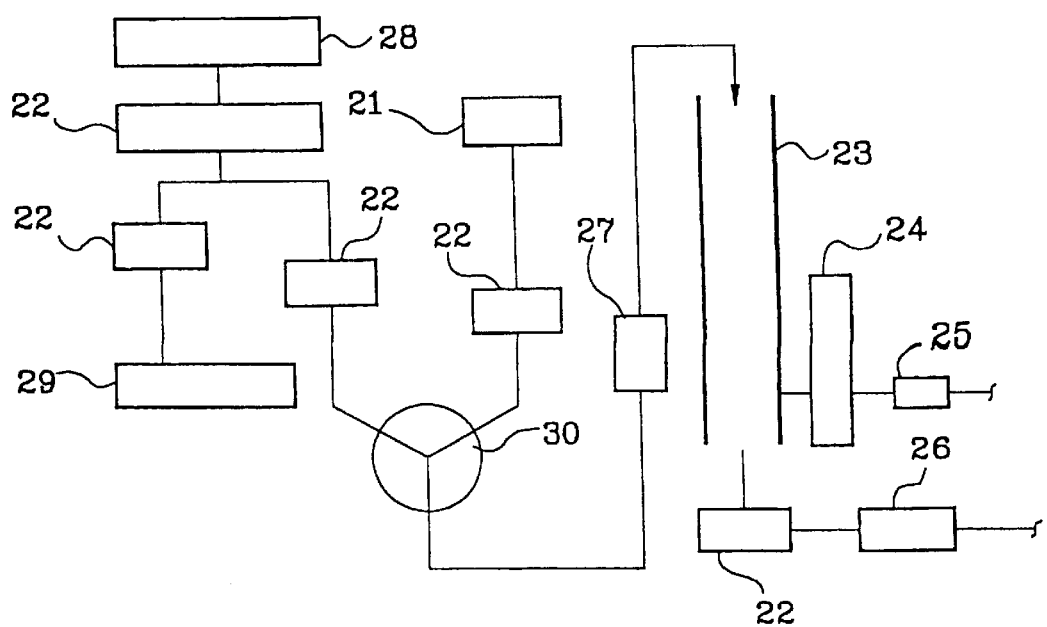
FIG. 6 is a schematic representation of a second embodiment of a system used for analyzing water-soluble contaminants in accordance with the present invention.

In another more preferred embodiment, the controller 27 comprises a humidifier. Additionally, as shown in FIG. 6, a flow selection valve 30 is present between reference air inlet 21 and condenser 23. A standard analysis gas supply source 29 and a clean air supply source 28 are also included and are in fluid communication with the flow control valve 22. The standard analysis gas supply source 29 is present in order to adjust analyzer 25 to allow for the analysis of water formed in the condenser 23. The analyzer is capable of functioning accurately by employing a high purity standard gas which is used in calibrating the analyzer. By supplying a known standard analysis gas at a specified concentration level, analyzer 25 may be adjusted. As an example, $SO_2$ may be used as a standard analysis gas.

The clean air supply source 28, which is in fluid communication with the standard analysis supply source 29 is capable of functioning as a means for controlling the concentration of the standard analysis gas. Specifically, the concentration of the standard analysis gas may be manipulated by adjusting the mixing rate of the standard analysis gas and the clean air. As a result, the analyzer 25 is adjusted.

Preferably, the standard analysis gas supply source and the clean air supply source are in fluid communication such that the standard analysis gas is mixed in advance with clean air to adjust the concentration of standard analysis gas to form a mixed analysis gas. The mixed analysis gas is typically supplied into the condenser through the flow selection valve 30. In view of the above, the analyzing capacity of the analyzer 25 may be adjusted by manipulating the mixing rate of the standard analysis gas and the clean air.

The flow selection valve 30 is preferably present in the form of a conventional three-way valve. The operator of the apparatus is then able to adjust the analyzer 25 using the standard analysis gas or analyze the reference air by positioning the three-way valve in the proper manner.

The invention will now be described in greater detail with reference to the examples which follow. It should be understood that the examples are set forth only to illustrate the invention, and are not meant as a limitation thereof.

EXAMPLE 1

An apparatus in accordance with the invention is used to analyze water-soluble contaminants present in the atmosphere of a semiconductor clean room. The reference air is in the form of fresh air with a temperature of 23.5° C.±0.5° C. and a humidity of 45±2%. Water is condensed from the reference air at a rate of 2.5 l/min. 10 μl of water is collected and analyzed using an ion chromatograph sold by Altech Co. based in the U.S.A. The Altech ion chromatographer comprises HPIC-AG4A-SC (P/N 037042), HPIC-AS4A-SC (P/N 043174) sold by the Dionex Co., an atomic suppressor (ASRS) for supplying regenerate after electrolytic dissociation of water, and a conductivity detector. An injection valve (P/N 038532) sold by the Dionex Co. is employed, and Model No. CD-03 sold by Chrontrol Co. is employed as an injection control timer.

Various contaminants such as sulfur dioxide, hydrochloric acid, and nitric acid were collected at a rate of 95% relative to the levels present in the reference air. The relative standard deviation of sulfur dioxide with a concentration of 10 ppb is 0.8%.

Example 2

An apparatus similar to the one described in Example 1 is employed. Water is condensed from the reference air at a rate of 5.0 l/min with 20 μl of water being eventually collected. The analyzer was found capable of analyzing the contaminants at this condensation rate.

In this example, the contaminants were collected at a rate of 95% with a relative standard deviation of 0.8%.

The invention is advantageous relative to the prior art in that water-soluble contaminants may be analyzed with a higher level of reliability than previously experienced.

In the drawings, examples, and specification, there have been disclosed typical preferred embodiments of the invention and, although specific terms are employed, they are used in a generic and descriptive sense only and not for purposes of limitation, the scope of the invention being set forth in the following claims.

That which is claimed:

1. A method of analyzing water-soluble contaminants in a cleanroom atmosphere, said method comprising:

providing a reference air stream from the cleanroom atmosphere to an analyzer, said reference air stream having gaseous water present therein;

maintaining the reference air stream at a constant temperature; then condensing the reference air stream at a condenser such that the gaseous water liquefies, said condenser being located between a reference air inlet and the analyzer; and supplying the liquefied water to the analyzer to analyze water-soluble contaminants in the cleanroom atmosphere.

2. A method according to claim 1, further comprising the step of conducting qualitative and quantitative analyses of the liquefied water in the analyzer.

3. A method according to claim 1, wherein the analyzer is an ion-exchange chromatographer.

4. A method according to claim 1, wherein the temperature of the reference air stream is maintained at a temperature ranging, from about 20° C. to about 40° C.

5. A method of analyzing water-soluble contaminants in a cleanroom atmosphere, said method comprising:

providing a reference air stream from the cleanroom atmosphere having gaseous water present therein;

controlling the humidity of the reference air stream; then condensing the controlled humidity reference air stream such that the gaseous water liquefies; and supplying the liquefied water to an analyzer to analyze water-soluble contaminants in the cleanroom atmosphere.

6. A method according to claim 5, wherein said controlling step comprises humidifying the reference air stream.

7. A method according to claim 5, wherein the humidity of the reference air stream is controlled to between about 30 percent and about 90 percent during said controlling step.

8. A method according to claim 5, wherein the humidity of the reference air stream is controlled to between about 35 percent and about 60 percent during said controlling step.

9. A method according to claim 5, wherein the humidity of the reference air stream is controlled to between about 40 percent and about 50 percent during said controlling step.

10. A method according to claim 1, wherein the condenser has a collector to gather the gaseous water and a water outlet to discharge the liquified water.

11. A method according to claim 1, wherein an amount of the reference air stream is controlled by a mass flow controller.

12. A method according to claim 1, wherein the condenser has a cooling medium for maintaining the constant temperature.

13. A method of analyzing water-soluble contaminants in a cleanroom atmosphere, said method comprising:

adjusting an analyzer using a standard analysis gas supply source;

providing a reference air stream from the cleanroom atmosphere to the analyzer, said air stream having gaseous water present therein;

maintaining the reference air stream at a constant temperature;

condensing the reference air stream at a condenser such that the gaseous water liquefies, said condenser being located between a reference air inlet and the analyzer; and supplying the liquefied water to the analyzer to analyze water-soluble contaminants in the cleanroom atmosphere.

14. A method according to claim 13, wherein the condenser has a collector to gather the gaseous water and a water outlet to discharge the liquefied water.

15. A method according to claim 13, wherein said step of adjusting the analyzer includes the step of calibrating the analyzer using the standard analysis gas supply source and a clean air supply source.

16. A method according to claim 13, further comprising the step of controlling the humidity of the reference air stream prior to said condensing step.

17. A method according to claim 16, wherein said controlling step comprises humidifying the reference air stream.

18. A method according to claim 17, wherein the humidity of the reference air stream is controlled by a humidifier.

19. A method according to claim 16, wherein the humidity of the reference air stream is controlled to between about 30 percent and about 90 percent during said controlling step.

20. A method according to claim 16, wherein the humidity of the reference air stream is controlled to between about 35 percent and about 60 percent during said controlling step.

21. A method according to claim 16, wherein the humidity of the reference air stream is controlled to between about 40 percent and about 50 percent during said controlling step.

* * * * *